United States Patent

Büchel et al.

[11] 4,237,142
[45] Dec. 2, 1980

[54] COMBATING FUNGI WITH 2-CARBAMOYLOXY-3,3-DIMETHYL-1-PHENOXY-1-(1,2,4-TRIAZOL-1-YL)-1-BUTANES

[75] Inventors: Karl H. Büchel; Wolfgang Krämer, both of Wuppertal; Wilhelm Brandes, Leichlingen, all of Fed. Rep. of Germany

[73] Assignee: Bayer Aktiengesellschaft, Leverkusen, Fed. Rep. of Germany

[21] Appl. No.: 971,291

[22] Filed: Dec. 20, 1978

[30] Foreign Application Priority Data

Jan. 7, 1978 [DE] Fed. Rep. of Germany ....... 2800544

[51] Int. Cl.$^3$ .................... A01N 43/64; C07D 249/08
[52] U.S. Cl. .................................... 424/269; 424/232; 424/245; 548/101; 548/262
[58] Field of Search ......................... 424/269; 548/262; 260/308 R

[56] References Cited

U.S. PATENT DOCUMENTS 4,145,428  3/1979  Kramer et al. ................ 260/308 R

FOREIGN PATENT DOCUMENTS 2600799  7/1977  Fed. Rep. of Germany ...... 260/308 R

Primary Examiner—Alton D. Rollins
Attorney, Agent, or Firm—Sprung, Felfe, Horn, Lynch & Kramer

[57] ABSTRACT

2-Carbamoyloxy-3,3-dimethyl-1-phenoxy-1-(1,2,4-triazol-1-yl)-1-butanes of the formula

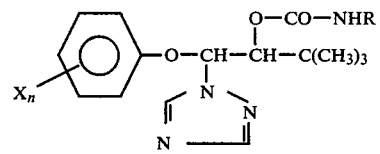

in which
R is alkyl, halogenoalkyl, alkoxycarbonyl, alkoxyalkyl, substituted phenyl or alkylsulphonyl-alkenyl-carbamoyl,
X each independently is halogen, alkyl, cycloalkyl, alkoxy, halogenoalkyl, alkylthio, alkoxycarbonyl, optionally substituted phenyl, optionally substituted phenoxy, optionally substituted phenylalkyl, amino, cyano or nitro, and
n is 0, 1, 2, 3, 4 or 5, as the free base, salt or metal salt complex thereof which possess fungicidal properties.

9 Claims, No Drawings

COMBATING FUNGI WITH 2-CARBAMOYLOXY-3,3-DIMETHYL-1-PHENOXY-1-(1,2,4-TRI AZOL-1-YL)-1-BUTANES

The present invention relates to and has for its objects the provision of particular new 2-carbamoyloxy-3,3-dimethyl-1-phenoxy-1-(1,2,4-triazol-1-yl)-1-butanes which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has already been disclosed that acylated triazolyl-O,N-acetals, such as, in particular, 2-alkylcarbonyloxy-3,3-dimethyl-1-phenoxy-1-(1,2,4-triazol-1-yl)-butanes substituted in the phenyl part, have good fungicidal properties (see DT-OS (German Published Specification) 2,600,799). However, their action is not always completely satisfactory, especially when low amounts and low concentrations are used. Furthermore, it has been generally known for a relatively long time that zinc ethylene-1,2-bis-dithiocarbamidate is a good agent for combating fungal diseases of plants (see Phytopathology 33, 1113, (1963)). However, it is possible to use it only to a limited extent, since in some cases it is of low activity when low amounts and concentrations are used.

The present invention provides, as new compounds, the carbamoyl-triazolyl-O,N-acetals of the general formula

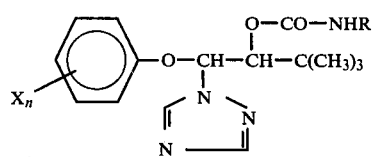

in which
R represents alkyl, halogenoalkyl, alkoxycarbonyl, alkoxyalkyl, substituted phenyl or alkylsulphonylalkenyl-carbamoyl,
X represents halogen, alkyl, cycloalkyl, alkoxy, halogenoalkyl, alkylthio, alkoxycarbonyl, optionally substituted phenyl, optionally substituted phenoxy, optionally substituted phenylalkyl, amino, cyano or nitro and
n represents 0, 1, 2, 3, 4 or 5, the substituents X being selected independently of each other when n is 2 or more.

The compounds, which may be used in the form of their acid addition salts or metal salt complexes have powerful fungicidal properties.

Preferably, R represents straight-chain or branched alkyl with 5 to 12 carbon atoms, halogenoalkyl with up to 4 carbon atoms and up to 5 identical or different halogen atoms (especially fluorine atoms and chlorine atoms), alkoxycarbonyl with 1–4 carbon atoms in the alkyl part, alkoxyalkyl with 1 to 4 carbon atoms in each alkyl part, or alkylsulphonyl-alkenyl-carbamoyl with 1 to 4 carbon atoms in the alkyl part and 2 to 4 carbon atoms in the alkenyl part, or represents monosubstituted or polysubstituted phenyl, each substituent being selected independently from straight-chain or branched alkyl with 1 to 4 carbon atoms, alkoxy and alkylthio with in each case 1 or 2 carbon atoms, halogenoalkyl with up to 2 carbon atoms and up to 5 identical or different halogen atoms (especially fluorine atoms and chlorine atoms) and alkoxycarbonylalkenyl with 1 to 4 carbon atoms in the alkyl part and 2 to 4 carbon atoms in the alkenyl part, X represents halogen, amino, cyano, nitro, straight-chain or branched alkyl with up to 4 carbon atoms, cycloalkyl with 5 to 7 carbon atoms (especially cyclohexyl), halogenoalkyl with up to 2 carbon atoms and up to 5 halogen atoms (especially fluorine atoms and chlorine atoms), alkoxycarbonyl with a total of up to 5 carbon atoms, alkoxy with 1 or 2 carbon atoms, alkylthio with 1 or 2 carbon atoms, or phenyl or phenoxy, either of which is optionally substituted by halogen, amino, cyano, nitro or alkyl with 1 to 2 carbon atoms, or represents phenylalkyl with 1 or 2 carbon atoms in the alkyl part, which is optionally substituted in the alkyl part by alkylcarbonyloxy with a total of up to 3 carbon atoms and which is optionally substituted in the phenyl part by halogen, nitro or cyano, and
n represents 0, 1, 2 or 3.

The compounds of the formula (I) have two asymmetric carbon atoms; they can therefore exist in the erythro form and in the threo form. In both cases, they are predominantly in the form of racemates.

Surprisingly, the carbamoyl-triazolyl-O,N-acetals according to the invention exhibit a considerably higher fungicidal activity than the acylated triazolyl-O,N-acetals known from the state of the art, such as, in particular, 2-alkylcarbonyloxy-3,3-dimethyl-1-phenoxy-1-(1,2,4-triazol-1-yl)-butanes substituted in the phenyl part, which are very closely related compounds chemically and from the point of view of their action, and than zinc ethylene-1,2,-bisdithiocarbamidate, which is a known substance of the same type of action.

The invention also provides a process for the preparation of a carbamoyl-triazolyl-O,N-acetal of the formula (I), in which a triazolyl derivative of the general formula

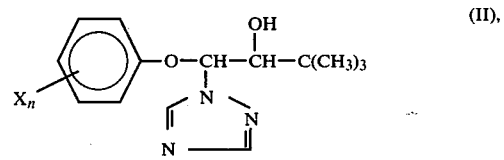

in which
X and n have the meanings stated above, (a) is reacted with an isocyanate of the general formula

in which
R has the meaning stated above, in the presence of a solvent and optionally in the presence of a catalyst, or (b) is reacted with a substituted 1,3,4-dioxazol-2-one of the formula

in which

R has the meaning stated above, in the presence of a solvent and optionally in the presence of a catalyst.

Furthermore, the carbamoyl-triazolyl-O,N-acetals of the formula (I) obtainable according to the invention can be converted into salts by reaction with acids, or the corresponding metal complexes can be obtained by reaction with metal salts.

If 1-(4-biphenylyloxy)-3,3-dimethyl-1-(1,2,4-triazol-1-yl)-butan-2-ol and methoxymethyl isocyanate are used as starting materials in process variant (a), the course of the reaction can be represented by the equation which follows:

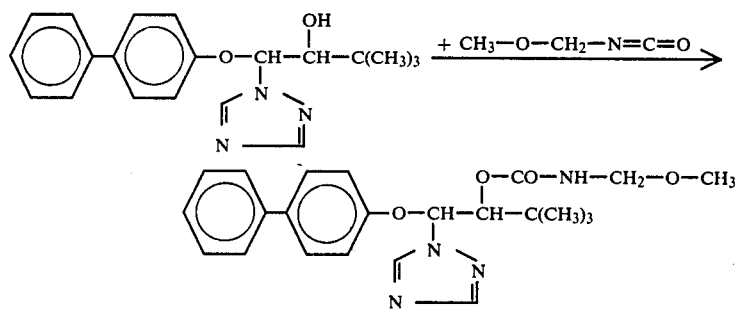

If 1-(4-biphenylyloxy)-3,3-dimethyl-1-(1,2,4-triazol-1-yl)-butan-2-ol and 5-methoxymethyl-1,3,4-dioxazol-2-one are used as starting materials in process variant (b), the course of the reaction can be represented by the equation which follows:

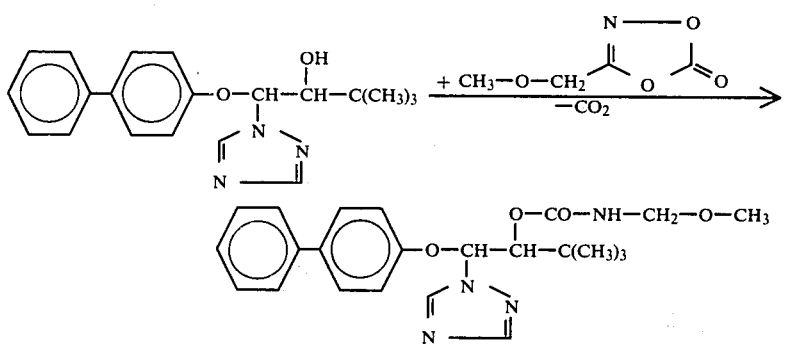

Starting materials of the formula (II) are known (see German Published Specification No. 2,324,010) and can be obtainee by the processes already described, for example by reducing the corresponding ketone derivatives with aluminum isopropylate or with complex hydrides in the presence of a solvent.

Isocyanates of the formula (III) are known and can be prepared by processes which are generally customary and known, for example by reacting amines with phosgene and subsequently heating the product.

1,3,4-Dioxazol-2-ones of the formula (IV) are known (see G. Beck, Chem. Ber., 84, 688 (1951) and can be prepared for example by reacting corresponding hydroxycarboxylic acids or acid hydrazides with phosgene at the boil.

Preferred possible solvents for the reaction according to process variant (a) are all the inert organic solvents, especially ketones, such as diethyl ketone, and in particular acetone and methyl ethyl ketone; nitriles, such as propionitrile, and in particular acetonitrile; ethers, such as tetrahydrofuran or dioxane; esters, such as ethyl acetate; aromatic hydrocarbons, such as benzene or toluene; and halogenated hydrocarbons, such as methylene chloride, carbon tetrachloride or chloroform.

Preferred catalysts which can be used in process variant (a) are tertiary bases, such as triethylamine and pyridine, or organotin compounds, such as dibutyl-tin dilaurate.

The reaction temperatures can be varied within a substantial range when carrying out the process variant (a). In general, the process is carried out at from 0° to 100° C., preferably at from 20° to 70° C.

In carrying out process variant (a), equimolar amounts of the reactants are preferably used. In order to isolate the compounds of the formula (I), the solvent is distilled off and the residue is worked up by customary methods.

Preferred possible solvents for the reaction according to process variant (b) are inert organic solvents, especially the solvents which have already been mentioned in the case of process variant (a).

Preferred catalysts which can be used in process variant (b) are tertiary amines, such as, for example, triethylamine, or alkali metal salts of fatty acids, such as, for example, sodium acetate.

The reaction temperatures can be varied within a substantial range in carrying out process variant (b). In general, the process is carried out at from 60° to 150° C., preferably at from 80° to 100° C.

In carrying out process variant (b), equimolar amounts of the reactants are preferably used. In order to isolate the compounds of the formula (I), the solvent is distilled off and the residue is worked up by customary methods.

As indicated above, the compounds (I) can be converted into acid-addition salts and metal salt complexes; it is preferred that these be physiologically acceptable.

It is possible to use all the physiologically acceptable acids for the preparation of acid addition salts of the compounds of the formula (I). Preferred acids include the hydrogen halide acids (for example hydrobromic acid and, especially, hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acids (for example p-toluenesulphonic acid and 1,5-naphthalenedisulphonic acid).

The salts of the compounds of the formula (I) can be obtained in a simple manner by customary salt-formation methods, for example by dissolving a compound of the formula (I) in a suitable inert solvent and adding the acid, for example hydrochloric acid, and they can be isolated in a known manner, for example by filtration, and optionally purified by washing with an inert organic solvent.

Possible salts for the preparation of metal salt complexes of the compounds of the formula (I) are preferably salts of metals of main groups II to IV and of subgroups I and II and IV to VIII, examples of metals which may be mentioned being copper, zinc, manganese, magnesium, tin, iron and nickel. Possible anions of the salts are those which are derived from physiologically acceptable acids, preferably the hydrogen halide acids (for example hydrochloric acid and hydrobromic acid), phosphoric acid, nitric acid and sulphuric acid.

The metal salt complexes of the compounds of the formula (I) can be obtained in a simple manner by customary processes, for example by dissolving the metal salt in alcohol, for example ethanol, and adding the solution to the compound of the formula (I). Metal salt complexes can be isolated in a known manner, for example by filtration, and optionally purified by recrystallisation.

Particularly active compounds according to the invention, in addition to those given in the preparative examples hereinbelow, are for example: 1-(4-chlorophenoxy)-3,3-dimethyl-2-methoxymethyl-carbamoyloxy-1-(1,2,4-triazol-1-yl)-butane, 1-(2,4-dichlorophenoxy)-3,3-dimethyl-2-methoxymethylcarbamoyloxy-1-(1,2,4-triazol-1-yl)-butane, 1-(4-chlorophenoxy)-3,3-dimethyl-2-trifluoromethylcarbamoyloxy-1-(1,2,4-triazol-1-yl)-butane and 1-(4-biphenylyloxy)-3,3-dimethyl-2-trifluoromethylcarbamoyloxy-1-(1,2,4-triazol-1-yl)-butane.

The active compounds according to the invention exhibit a powerful fungitoxic action. They do not damage crop plants in the concentrations required for combating fungi. For these reasons, they are suitable for use as plant protection agents for combating fungi. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which attack above-ground parts of plants or which attack the plants through the soil, as well as against seed-borne pathogens. They develop a particularly good activity against parasitic fungi on above-ground parts of plants.

As plant protection agents, the active compounds according to the invention can be used with particularly good success for combating species of Venturia, for example against the apple scab causative organism (*Fusicladium dendriticum*), and species of Uromyces, such as, for example, the bean rust causative organism (*Uromyces phaseoli*), and for combating species of Phytophthora and cereal diseases.

As plant protection agents, the active compounds according to the invention can be used for the treatment of seed or soil and for the treatment of above-ground parts of plants.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other active compounds, such as fungicides, insecticides, acaricides, nematicides, herbicides, bird repellents, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomizing, dusting, scattering, dry dressing, moist dressing, wet dressing, slurry dressing or encrusting.

Especially when used as leaf fungicides, the active compound concentrations in the use forms can be varied within a substantial range. They are, in general, from 0.1 to 0.00001 percent by weight, preferably from 0.05 to 0.0001%.

In the treatment of seed, amounts of active compound of 0.001 to 50 g, preferably 0.01 to 10 g, are generally employed per kilogram of seed.

For the treatment of soil, amounts of active compound of 1 to 1000 g, in particular 10 to 200 g, are generally employed per cubic meter of soil.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further providces crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

EXAMPLE 1

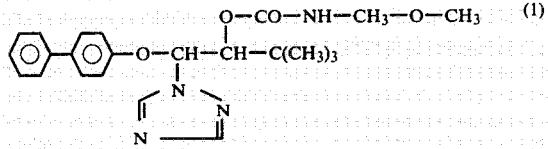

505 g (1.5 moles) of 1-(4-biphenylyloxy)-3,3-dimethyl-1-(1,2,4-triazol-1-yl)-butan-2-ol (A form) and 140 g (1.6 moles) of methoxymethyl isocyanate were heated under reflux in 2.5 liters of tetrahydrofuran in the presence of 40 ml of triethylamine and 1 ml of dibutyl-tin dilaurate for 48 hours. Thereafter, the solvent was stripped off in vacuo and 3 liters of petroleum ether were added to the residue. The crystalline precipitate formed was extracted by stirring with 1.5 liters of diisopropyl ether. 528 g (82.5% of theory) of 1-(4-biphenylyloxy)-3,3-dimethyl-2-methoxymethylcarbamoyloxy-1-(1,2,4-triazol-1-yl)-butane (A form) of melting point 95°–98° C. were obtained.

The compounds of Table 1 which follows were obtained analogously.

TABLE 1

| Compound No. | $X_n$ | R | Melting point (°C.) |
|---|---|---|---|
| 2 | 4-phenyl | —(CH$_2$)$_2$—Cl | 138–41 (B-Form) |
| 3 | 4-phenyl | —CO—OCH$_3$ | 184–85 (B-Form) |
| 4 | 4-phenyl | —CO—OC$_2$H$_5$ | 164–66 (B-Form) |

TABLE 1-continued

[Structure: X_n-phenyl-O-CH(N-triazolyl)-CH(O-CO-NHR)-C(CH3)3]

| Compound No. | X_n | R | Melting point (°C.) |
|---|---|---|---|
| 5 | 4-phenyl | —(CH$_2$)$_2$—Cl | 103–05 (A-Form) |
| 6 | 4-phenyl | —CO—OCH$_3$ | 120 (A-Form) |
| 7 | 4-phenyl | —CO—OC$_2$H$_5$ | 100 (A-Form) |
| 8 | 4-phenyl | —CH$_2$—O—CH$_3$ | 141–44 (B-Form) |
| 9 | 4-phenyl | —CO—N(SO$_2$CH$_3$)(CH$_2$—CH=CH$_2$) | 141–44 (B-Form) |
| 10 | 4-phenyl | —(CH$_2$)$_2$—CH(CH$_3$)—CH$_2$—C(CH$_3$)$_3$ | 109–15 (B-Form) |
| 11 | 4-phenyl | phenyl-CH=CH—COOCH$_3$ | 194–200 |
| 12 | 4-phenyl | 2,6-(CH$_3$, i-C$_3$H$_7$)-phenyl | 158–65 |
| 13 | 4-phenyl | 4-C(CH$_3$)$_3$-phenyl | 193–206 |
| 14 | 4-phenyl | 2-CH$_3$, 4-OCH$_3$-phenyl | 148–55 |
| 15 | 4-Cl | —CO—OCH$_3$ | 151–54 (A-Form) |
| 16 | 4-phenyl | —CH$_2$—O—C$_2$H$_5$ | 140(×HCl) (Base 115° C.) |

TABLE 1-continued

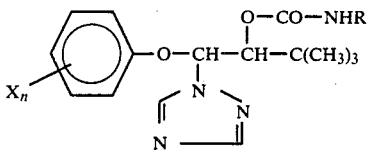

| Compound No. | $X_n$ | R | Melting point (°C.) |
|---|---|---|---|
| 17 | 4-(phenyl) | —(CH$_2$)$_3$—O—CH$_3$ | 100(×HCl) |

NOTE:
A form and B form = in each case one of the two possible geometric isomers.

The fungicidal activity of the compounds of this invention is illustrated by the following examples wherein the compounds according to the present invention are each identified by the number (given in brackets) from preparative Example 1 hereinabove:

EXAMPLE 2

Fusicladium test (apple)/protective

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated amount of emulsifier.

Young apple seedlings in the 4-6 leaf stage were sprayed with the spray liquid until dripping wet. The plants remained in a greenhouse for 24 hours at 20 degrees C. and at a relative atmospheric humidity of 70%. They were then inoculated with an aqueous conidium suspension of the apple scab causative organism (Fusicladium dendriticum) and incubated for 18 hours in a humidity chamber at 18-20 degrees C. and at a relative atmospheric humidity of 100%.

The plants were then brought into a greenhouse again for 14 days.

15 days after inoculation, the infection of the seedlings was determined. In this test compounds 1, 2, 8, 16 and 17 exhibited a very good action which was distinctly superior to that of the compounds known from the prior art.

EXAMPLE 3

Uromyces test (bean rust)/protective

Solvent: 4.7 parts by weight of acetone
Emulsifier: 0.3 part by weight of alkylaryl polyglycol ether
Water: 95 parts by weight The amount of active compound required for the desired concentration of active compound in the spray liquor was mixed with the stated amount of the solvent and the concentrate was diluted with the stated amount of water which contained the stated amount of emulsifier.

The young bean plants, which were in the 2-leaf stage, were sprayed with the spray liquor until dripping wet. The plants remained in a greenhouse for 24 hours at 20-22 deg. C. and a relative atmospheric humidity of 70% in order to dry. They were then inoculated with an aqueous uredospore suspension of the causative organism of bean rust (Uromyces phaseoli) and incubated for 24 hours in a dark humidity chamber at 20-22 deg. C. and 100% relative atmospheric humidity.

The plants were then set up in a greenhouse under intensive illumination for 9 days at 20-22 deg. C. and a relative atmospheric humidity of 70-80%.

10 days after the inoculation, the infection of the plants was determined. In this test compounds 1-11 and 13-17 exhibited a very good action which was distinctly superior to that of the compounds known from the prior art.

EXAMPLE 4

Phytophthora test (tomato)/protective

Solvent: 4.7 parts by weight of acetone
Emulsifier: 0.3 part by weight of alkylaryl polyglycol ether
Water: 95 parts by weight The amount of the active compound required for the desired concentration of the active compound in the spray liquid was mixed with the stated amount of solvent and the concentrate was diluted with the stated amount of water which contained the stated additions.

Young tomato plants with 2 to 4 foliage leaves were sprayed with the spray liquid until dripping wet. The plants remained in a greenhouse for 24 hours at 20 deg. C. and at a relative atmospheric humidity of 70%. The tomato plants were then inoculated with an aqueous spore suspension of Phytophthora infestans. The plants were brought into a moist chamber with an atmospheric humidity of 100% and a temperature of 18-20 deg. C.

After 5 days the infection of the tomato plants was determined. In this test compounds 1, 5, 8, 16 and 17 exhibited a very good action which was distinctly superior to that of the compounds known from the prior art.

It will be appreciated that the instant specification and examples are set forth by way of illustration and not limitation, and that various modifications and changes may be made without departing from the spirit and scope of the present invention.

What we claim is:

1. A 2-carbamoyloxy-3,3-dimethyl-1-phenoxy-1-(1,2,4-triazol-1-yl)-butane of the formula

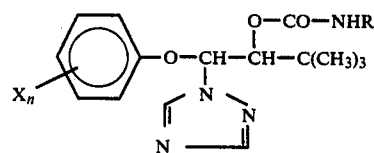

in which
- R is halogenoalkyl with up to 4 carbon atoms and up to 5 halogen atoms, alkoxycarbonyl with 1–4 carbon atoms in the alkyl part, alkoxyalkyl with 1 to 4 carbon atoms in each alkyl part, alkylsulphonylalkenyl-carbamoyl with 1 to 4 carbon atoms in the alkyl part and 2 to 4 carbon atoms
- X each independently is halogen, amino, cyano, nitro, alkyl with up to 4 carbon atoms, cycloalkyl with 5 to 7 carbon atoms, halogen-alkyl with up to 2 carbon atoms and up to 5 halogen atoms, alkoxy with 1 to 2 carbon atoms, phenyl, phenoxy, phenyl or phenoxy substituted by halogen, amino, cyano, nitro or alkyl with 1 to 2 carbon atoms, or phenyl-alkyl with 1 or 2 carbon atoms in the alkyl part which is optionally substituted in the phenyl by halogen, nitro or cyano, and
- n is 0, 1, 2, 3, 4 or 5.

2. A compound according to claim 1, in which n is 0,1,2 or 3.

3. A compound according to claim 1, wherein such compound is 1-(4-biphenylyloxy)-3,3-dimethyl-2-methoxymethylcarbamoyloxy-1-(1,2,4-triazol-1-yl)-butane of the formula

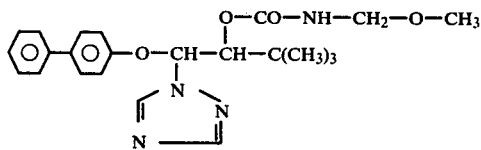

4. A compound according to claim 1, wherein such compound is 1-(4-biphenylyloxy)-3,3-dimethyl-2-(β-chloroethylcarbamoyloxy)-1-(1,2,4-triazol-1-yl)-butane of the formula

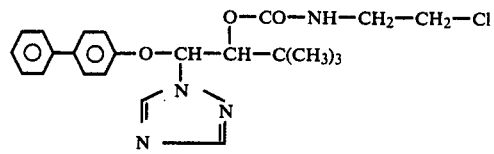

5. A compound according to claim 1, wherein such compound is 1-(4-biphenylyloxy-3,3-dimethyl-2-ethoxymethylcarbamoyloxy-1-(1,2,4-triazol-1-yl)-butane of the formula

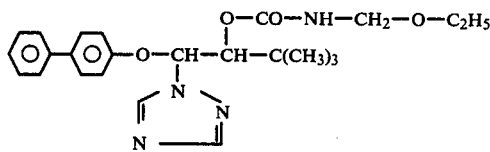

6. A compound according to claim 1, wherein such compound is 1-(4-biphenylyloxy-3,3-dimethyl-2-methoxypropylcarbamoyloxy-1-(1,2,4-triazol-1-yl)-butane of the formula

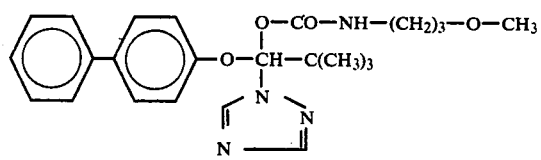

7. A fungicidal composition containing as active ingredient a fungicidally effective amount of a compound according to claim 1 in admixture with a diluent.

8. A method of combating fungi, which comprises applying to the fungi, or to a habitat thereof, a fungicidally effective amount of a compound according to claim 1.

9. The method according to claim 8, in which said compound is
1-(4-biphenylyloxy)-3,3-dimethyl-2-methoxymethylcarbamoyloxy-1-(1,2,4-triazol-1-yl)-butane,
1-(4-biphenylyloxy)-3,3-dimethyl-2-β-chloroethylcarbamoyloxy-1-(1,2,4-triazol-1-yl)-butane,
1-(4-biphenylyloxy)-3,3-dimethyl-2-ethoxymethylcarbamoyloxy-1-(1,2,4-triazol-1-yl)-butane or
1-(4-biphenylyloxy)-3,3-dimethyl-2-methoxypropylcarbamoyloxy-1-(1,2,4-triazol-1-yl)-butane.

* * * * *